United States Patent [19]

Rönnberg et al.

[11] Patent Number: 5,906,604
[45] Date of Patent: May 25, 1999

[54] ATTACHMENT MEANS FOR A BELT AND AN ABSORBENT ARTICLE

[75] Inventors: Peter Rönnberg, Mölndal; Olle Carlbark, Kållered; Björn Larsson, Billdal, all of Sweden

[73] Assignee: SCA Hygiene Products AB, Goteborg, Sweden

[21] Appl. No.: 08/947,746

[22] Filed: Oct. 9, 1997

Related U.S. Application Data

[63] Continuation of application No. 08/545,708, filed as application No. PCT/SE94/00414, May 6, 1994, abandoned.

[30] Foreign Application Priority Data

May 12, 1993 [SE] Sweden .................................. 93016931

[51] Int. Cl.⁶ ...................................................... A61F 13/15
[52] U.S. Cl. ........................... 604/386; 604/391; 604/392; 604/393; 2/338; 2/920
[58] Field of Search ..................... 604/391, 392, 604/393, 386, 387, 396; 2/338, 311, 312, 920

[56] References Cited

U.S. PATENT DOCUMENTS

| | | | |
|---|---|---|---|
| 3,955,575 | 5/1976 | Okuda | 604/391 |
| 4,700,406 | 10/1987 | Meistrell | 2/338 |
| 4,761,834 | 8/1988 | Kolb | 2/338 |
| 4,773,906 | 9/1988 | Krushel | 604/391 |
| 4,936,840 | 6/1990 | Proxmire | 604/391 |
| 4,944,043 | 7/1990 | Bush . | |
| 4,994,054 | 2/1991 | Pigneul et al. | 604/391 |
| 5,016,291 | 5/1991 | Capper | 2/920 |
| 5,135,522 | 8/1992 | Fehrenkrug et al. | 604/392 |
| 5,214,806 | 6/1993 | Flores | 2/312 |
| 5,309,575 | 5/1994 | Lookhoof | 2/920 |
| 5,318,555 | 6/1994 | Siebers et al. | 604/391 |
| 5,445,628 | 8/1995 | Gipson et al. | 604/392 |
| 5,549,593 | 8/1996 | Ygge et al. | 604/392 |
| 5,685,873 | 11/1997 | Bruemmer | 604/392 |

FOREIGN PATENT DOCUMENTS

| | | | |
|---|---|---|---|
| 2021538 | 1/1992 | Canada | 604/391 |
| 2586558 | 6/1987 | France . | |
| 2 232 337 | 12/1990 | United Kingdom . | |
| WO 91/08725 | 6/1991 | WIPO . | |

*Primary Examiner*—Mark O. Polutta
*Attorney, Agent, or Firm*—Burns, Doane, Swecker & Mathis LLP

[57] ABSTRACT

The invention relates to a belt (1) of flexible material for use with absorbent garments, wherein the belt comprises attachment means (6, 9, 10, 11, 21, 22) securely attached at one end. The attachment means is in the form of a flexible strip of hook elements such as used for releasable hook and loop type connectors and is used for securing that one end to an outer surface of the belt. In order to provide greater comfort for the wearer the attachment means itself is located approximately centrally and extends with its greatest dimension (a) in the width direction of the belt where dimension (a) is between 25% to 75% of the belt width (z).

17 Claims, 4 Drawing Sheets and, in particular, to a waist belt of flexible material comprising attachment means securely attached to the belt and located proximate one of the ends of said belt for securing said one end to an outer surface of said belt situated between the longitudinal edges thereof, said attachment means being of the hook element strip releasable type, and wherein said attachment means itself extends with its greatest dimension in the width direction of the belt.

ATTACHMENT MEANS FOR A BELT AND AN ABSORBENT ARTICLE

This application is a continuation of application Ser. No. 08/545,708, filed Nov. 7, 1995, now abandoned, which is a 371 of PCT/SE94/00414 filed May 6, 1994.

FIELD OF THE INVENTION

The invention relates to a belt of the type used with an absorbent garment and, in particular, to a waist belt of flexible material comprising attachment means securely attached to the belt and located proximate one of the ends of said belt for securing said one end to an outer surface of said belt situated between the longitudinal edges thereof, said attachment means being of the hook element strip releasable type, and wherein said attachment means itself extends with its greatest dimension in the width direction of the belt.

BACKGROUND OF THE INVENTION

The type of belt in question can be integrated with an absorbent garment worn to assist in the collection of bodily discharges, particularly for persons suffering from incontinence, or the belt can be a separate belt to which an absorbent garment portion is attached by some means of releasable attachment such as hook and loop (also called touch and close) type fastening means, for instance such as sold under the trademark "VELCRO".

The belt of the separate type can be either a disposable belt, for limited use with a small number of absorbent chassis garments and thus requiring no particular cleaning, or a more permanent type which may be washed many times before its effectiveness or appearance warrants a change to a new belt.

Absorbent garments of the above mentioned type are well known in the art.

WO-A-91/08725 discloses an example of both these types in conjunction with an absorbent garment.

One of the problems recognized with such belts is achieving maximum comfort for the user by correct fitting, since incorrect fitting will result in sore, cut and/or painful areas for the user.

One area where it has been found desirable to increase comfort is the area of the belt attachment to itself. When one examines WO-A-91/08725 for example, it is clear that the attachment of the hook element strip and the loop element strip together for fastening the belt can easily result in one of the edges of the hook strip projecting beyond the zone to which it is intended to be attached and, as a result, contacting the body. This contact with the body is particularly uncomfortable.

Where the problem of incontinence is involved, it will be appreciated that persons suffering from this problem are often old and have physical handicaps of various types. As a consequence, they often require the assistance of personnel for fitting the belts or garments with integrated belts. If they, or the assistant personnel do not fasten the belt with great care, the hook element strips can easily be left in a position which makes them contact the body. This factor is particularly important for the case where the users are unable to assist themselves or otherwise unable to communicate the poor fitment to the assistant personnel.

It is also known from GB-A-2 232 337 to use longitudinal strips for belt fastening, whereby the strip is placed lengthways along the length of the belt portion. In this way, the risk of the hook element strip contacting the body above or below the longitudinal edges of the belt portion is reduced. The extent of the strip in the longitudinal direction of the belt portion is consequently considerable in order to be able to achieve adequate shear strength of the releasable fastener. This brings with it however the disadvantage that the strips may not properly overlap and will thus contact the wearer's body although at a different location. Such is of particular importance where the belt is slightly too small for example.

Arrangement of the elongate strip of hook elements along the width of the belt is known per se from FR-A-2 586 558, where a small margin between the edges of the strip and the outer edges of the belt is left. However, the size of such margin was not of importance to the inventors thereof and was thus nowhere considered.

SUMMARY

The aforementioned problems relating to fitting and comfort when wearing absorbent garments of the aforementioned type are solved by the features of the belt according to the present invention. The present invention provides a waist belt for an absorbent garment, including a flexible material having first and second ends and longitudinal edges, a distance between the ends defining a length of the belt for securing the belt around a waist of a user of the absorbent garment. Attachment means securely attached to the belt and located proximate one of the ends of the belt are provided for securing one end thereof directly to an attachment zone defined by an outer surface of the belt situated between the longitudinal edges thereof, a distance between the longitudinal edges defining a width of the belt and a width of the attachment zone. The outer surface of the belt is formed of a loop material at least in the attachment zone of the outer surface of the belt at which the one end is to be attached. The attachment means is a hook element strip of a releasable type, which extends with its greatest dimension in a width direction of the belt, the greatest dimension of the attachment means is in the range of 25% to 75% of the width of the attachment zone taken at a location of the outer surface of the belt at which one end is to be attached to thereby reduce the risk of the attachment means contacting the user of the absorbent garment when the belt is secured around the waist of the user.

It should be noted that, while the term "absorbent garment" has been used in conjunction with incontinence, and particularly adult incontinence, the invention is not limited to this particular use or any particular size or particular type of absorbent garment implied thereby and it is clear for the skilled man that such belts could be used with baby's or children's diapers for example, merely by adapting the dimensions and materials appropriately.

BRIEF DESCRIPTION OF THE DRAWINGS

The invention will now be explained in more detail with reference to certain non-limiting embodiments and with reference to the accompanying drawings, in which.

DETAILED DESCRIPTION OF PREFERRED EMBODIMENTS

Figure 1:
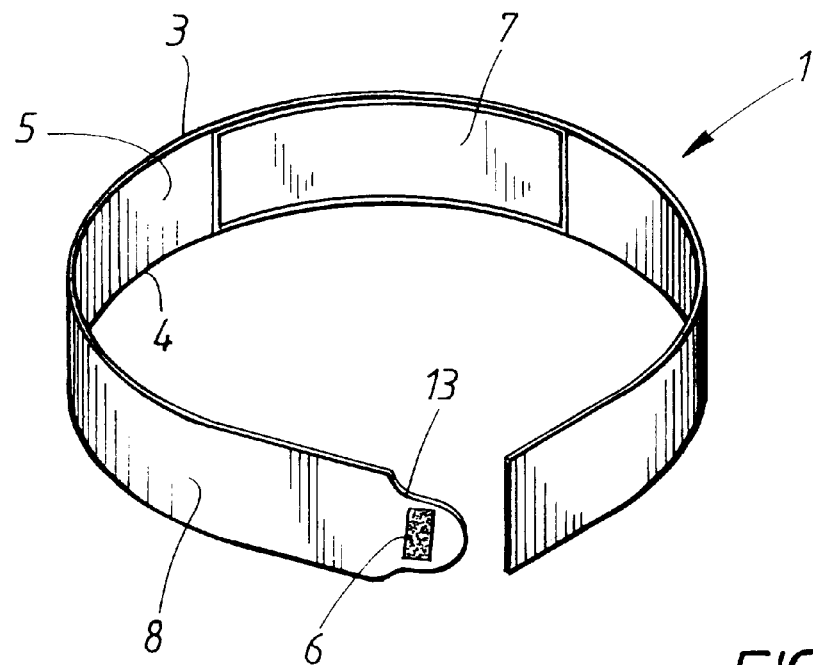
FIG. 1 depicts one embodiment of a separate belt in accordance with the invention whereby, for purposes of clarity, the belt is shown looped in the opposite manner to that obtained upon wearing.

FIG. 1 shows a belt generally denoted 1 which is made of flexible material such that it can be wrapped around a user's waist. The belt in FIG. 1 is shown, for reasons of clarity, wrapped around an imaginary center point in a manner opposite to that normally used when fitted to a user. Thus the inside of the belt 8 is here shown as if it were on the outside.

Figure 4:
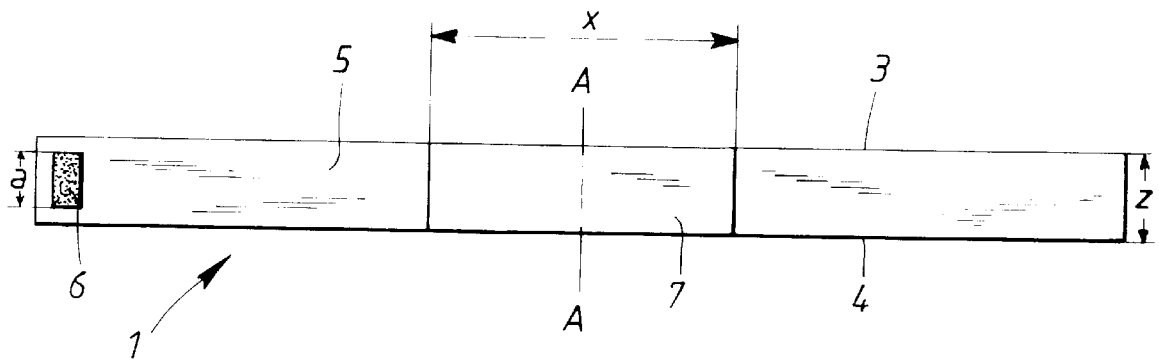
FIG. 4 shows a belt according to the invention laid out flat.

The belt is substantially rectangular in shape comprising two laterally spaced longitudinal edges 3 and 4 separated by a distance z (see FIG. 4). At one end, the belt is foreseen with an end portion 13 here shown as having a reduced width, on which end portion is securely affixed a flexible strip 6 having hook elements. This strip is of the type forming one half of the joining portions of a hook and loop type fastening means. The loop part of the joint in the embodiment shown is thus formed by the belt material itself.

Figure 3:
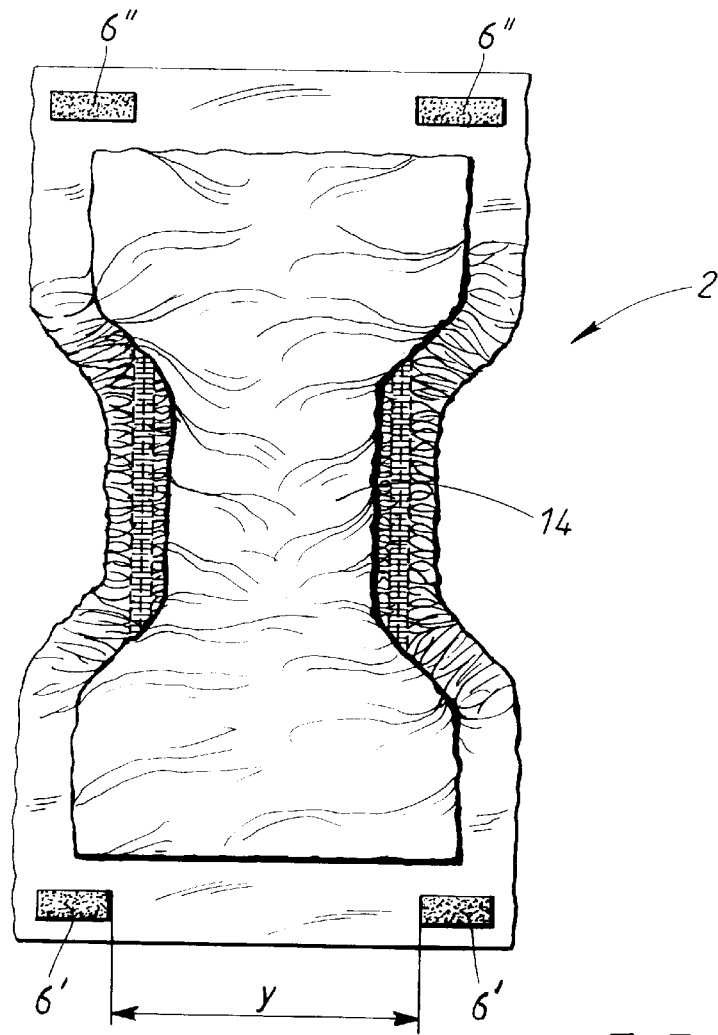
FIG. 3 shows an absorbent garment in the form of a chassis, adapted for fitting to the belt of the invention.

The outside surface 5 of the belt 1 (depicted in FIG. 1 as the inside) serves as an area of releasable attachment, partly for the strip 6 located at one end of the belt and also for similar strips 6' and 6" of a chassis 2 having absorbent material 14 therein (see FIG. 3).

On the outside surface 5 of the belt 1 there may also be a portion 7, formed by attaching a strip of suitable material to the outside surface 5 of the belt, to which the hook element strips 6' and 6" cannot attach.

The manner of fitting a chassis 2 to the separate belt 1 will now be briefly described. Firstly the belt is passed around the wearer's waist and the hook element strip 6 is pressed lightly onto the releasable attachment surface formed by the outside surface 5 to fasten it in place. The chassis portion is then attached to the outside of the belt behind the wearer's back by attaching the two strips 6' (or alternatively strips 6") to the belt surface 5. The free end of the garment is then passed between the wearer's legs and secured by means of the strips 6" to the front of the belt.

Figure 7:
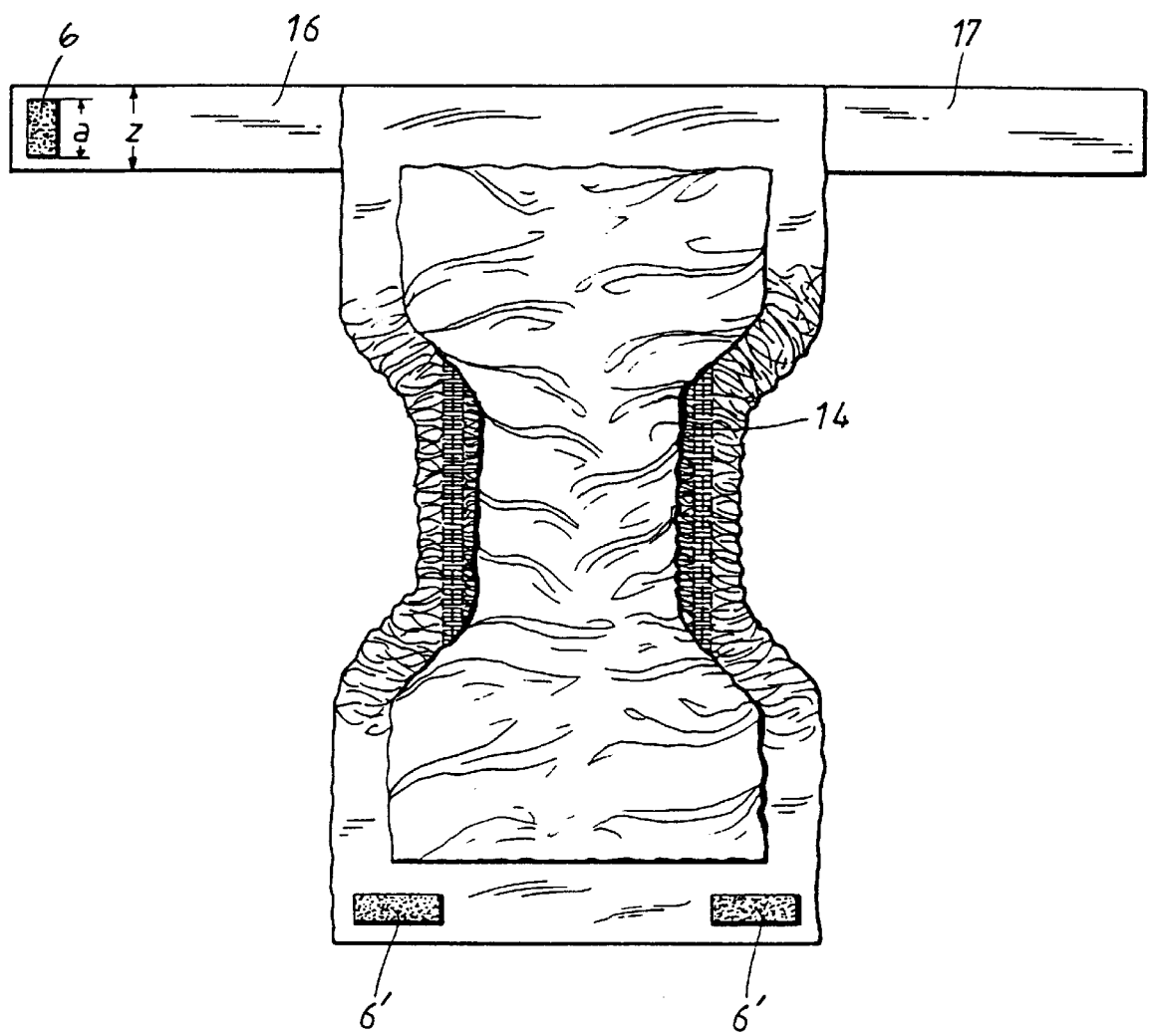
FIG. 7 shows an embodiment of an absorbent garment having an integrated belt in accordance with the invention.

The manner of fitting the garment shown in FIG. 7 having an integrated belt is the same as above, except that no attachment of any strips 6" is required.

In pressing the hook element strip 6 lightly into place, without the belt of the invention, it is easy not to take adequate care in preventing that the hook element strips project beyond the edges of the belt and thus touch the wearer. However, by using the belt of the invention this problem is obviated. Thus the strip 6 in FIG. 1 has a longitudinal extent "a" across the width of the belt which is between 25% and 75% of the width "z" thereof, preferably less than 60% and more preferably less than 50%.

Figure 2:
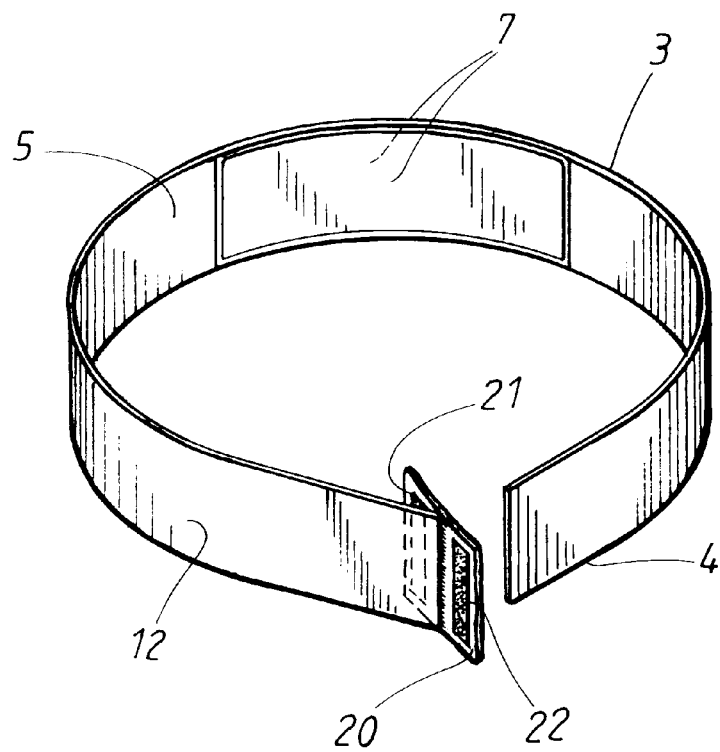
FIG. 2 depicts a further embodiment of a separate belt according to the invention wherein the belt is of the reversible type, capable of being used either way round.
Figure 5:
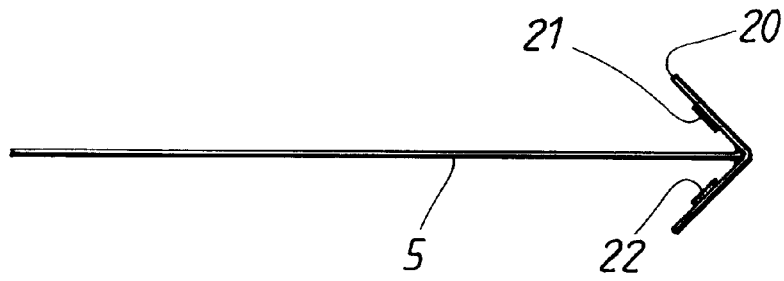
FIG. 5 shows a plan view of a reversible belt similar to that in FIG. 2.

A further embodiment of the invention is shown in FIG. 2 and FIG. 5 which each show a reversible belt. Corresponding zones 5 and 12 are provided for releasable attachment on either side with or without a zone 7 on either or both sides. At one end of the belt there is attached an extra piece 20 of flexible material, which has attached thereto two strips 21 and 22 of hook elements, similar to the element 6 of FIG. 1. Depending on which way round the belt is worn, either one or the other hook element strip 21 or 22 can be used for fastening the belt. Thus each of the two strips has a length of between 25% and 75% of the belt width "z".

Clearly advantageous with the use of such belts of the single sided type or the type which are integrated into an absorbent garment (see e.g. FIG. 7) is where at least some of the inner surface material of the belt is moisture-absorbent. When the belt is integrated into an absorbent garment, it exhibits two ends 16, 17 extending outwardly from the sides of the absorbent garment, one of which includes the hook element strip 6.

A woven material is normally used for both sides of a separate re-usable belt, or the outside of a disposable belt (integrated or not) due to its releasable attachability characteristics for hook element strips and also due to its washability.

However non-woven, cheaper materials for the outside of the belt can be used with a hook element strip attachable to non-woven materials.

In particular, when using non-woven materials for the releasable attachment surface of the belt it is possible to achieve particularly favorable peel strength and shear strength combinations, which give a peel strength of 0.1–2.0 $Ncm^{-1}$, preferably down to as low as 0.2–0.8 $Ncm^{-1}$, and a shear strength greater than 1 $Ncm^{-2}$, preferably greater than 15 $Ncm^{-2}$ and normally greater than 20 $Ncm^{-2}$. In this way, the strip of material can be made very thin and also with its largest dimension closer to 50% or even less of the belt width.

Figure 6A:
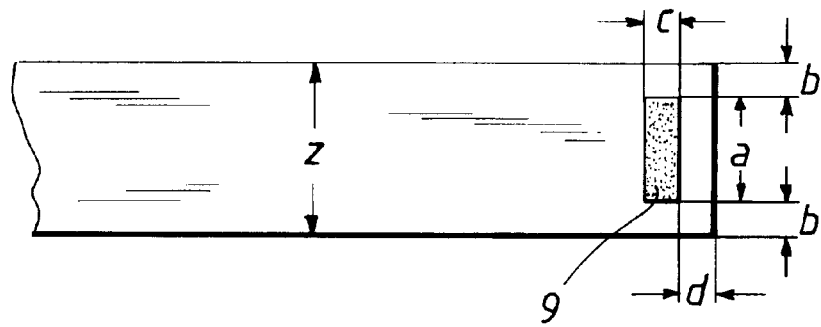
FIG. 6 shows three possible embodiments, in FIGS. 6(A), 6(B) and 6(C) of elongate hook element strips of the belt of the present invention.

As can be seen from FIG. 6, showing three possible strip embodiments 9, 10, and 11, the extent "a" between the outer edges of the strip(s) leaves a distance or margin "b" from each edge 3, 4 of the belt. The larger the distance "b", the less the risk that the strip portions 9, 10, or 11, will touch the wearer when the belt is fitted slightly incorrectly.

Figure 6B:
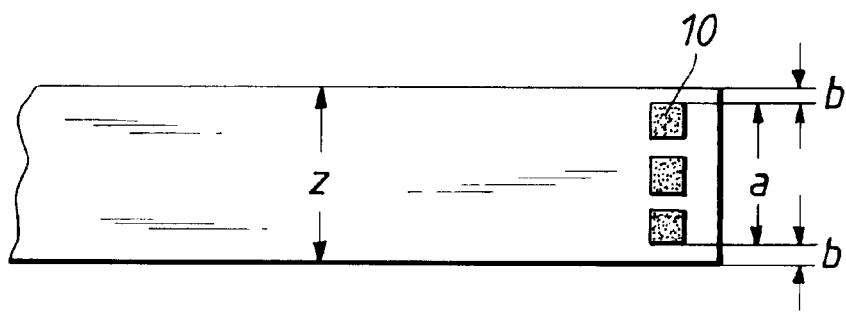
Figure 6C:
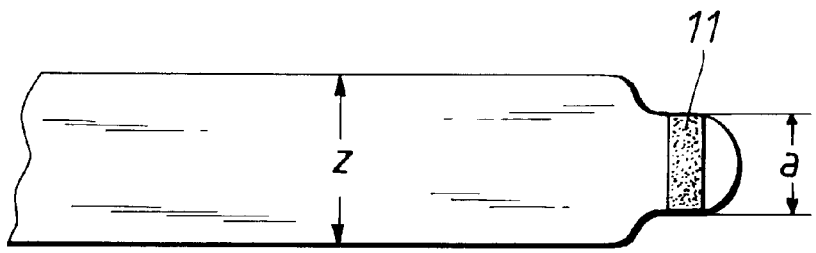

As can be seen, the strips are generally elongate, or in the case of a series of strips 10 as in FIG. 6(B), the series of strips is elongate. By elongate is meant that the dimension "a" is larger than dimension "c". Preferably a ratio of a:c greater than 2:1 is used and even more preferably a ratio of over 3:1. Thus, to achieve the aforementioned advantages, the strips with their larger dimension "a" are laid across the belt width (z), as depicted, to give the strips a dimension such that the larger dimension "a" has a length of between 25% and 75% of the width (z) of the main area (5) of the belt, which width (z) for adult incontinence applications lies between 70 to 160 mm. By width of the belt, is hereby meant the width of the belt at the zone where the strip 9, 10, 11 will attach. Thus in the embodiment of FIG. 6(C), although the strip 11 extends entirely across the reduced portion of the belt, the strip length "a" still lies within the stated range of values.

Whilst the embodiment of FIG. 6(B) shows three strips sections 10, it is clear that two or more than three could be used. However, it is the distance "a" between the outer edges of the outermost strips that is the dimension which must fall within the range 25% to 75%, preferably being less than 60%, or more preferably less than 50%.

As will be noted, the strips or series of strips are placed substantially in the middle of the belt width, such that the two margins "b" are substantially equal for any given belt.

The area denoted by "d" in FIG. 6(A) is a finger-grip portion of the end of the belt for unfastening the belt by simple lifting and consequent peeling of the hook element strip from where it is attached to the belt. By use of a thin strip, as described above and which has low peel strength, it is possible to reduce distance "d" to an absolute minimum, thus saving belt material and reducing cost.

Whilst particular embodiments of the invention have been described above, it is to be understood that these do not limit the scope of the invention which is defined by the claims appended hereto.

We claim:

1. A waist belt for an absorbent garment, comprising:
   a flexible material having first and second ends and longitudinal edges, a distance between said ends defining a length of said belt for securing said belt around a waist of a user of the absorbent garment,
   attachment means securely attached to the belt and located proximate one of the ends of said belt for securing said one end directly to an attachment zone defined by an outer surface of said belt situated between the longitudinal edges, a distance between the longitudinal edges defining a width of said belt and a width of said attachment zone, and the outer surface of said belt being formed of a loop material at least in the attachment zone of the outer surface of said belt at which said one end is to be attached,
   said attachment means being of a hook element strip releasable type, said attachment means extends with its greatest dimension in a width direction of the belt,
   the greatest dimension of said attachment means is in the range of 25% to 75% of the width of said attachment zone taken at a location of the outer surface of said belt at which said one end is to be attached to thereby reduce the risk of said attachment means contacting the user of the absorbent garment when said belt is secured around the waist of the user.

2. An absorbent garment incorporating the waist belt according to claim 1, wherein said belt is integrated into the absorbent garment such that the ends of the waist belt extend outwardly from sides of said absorbent garment.

3. Waist belt according to claim 1, wherein the width of said belt has a range of 70 to 160 mm.

4. Waist belt according to claim 1, wherein said attachment means is divided, in its longitudinal direction across the belt width, into a series of two or more separate strips, a longitudinal extent of said series being defined by outer edges of the strips closest to the longitudinal edges of the belt.

5. Waist belt according to claim 1, wherein the one end portion of the belt on which the attachment means is located has a width which lies between 40% to 80%, of the width of the belt.

6. Waist belt according to claim 1, wherein said greatest dimension of the attachment means is less than 60% of the belt width.

7. Waist belt according claim 1, wherein the greatest dimension of the attachment means in the width direction of the belt is more than 2 times, a lateral extent of said attachment means in the longitudinal direction of the belt.

8. Waist belt according to claim 1, wherein an the outer surface of the belt to which the attachment means releasably attaches, consists of a non-woven material, and that at least a part of the material on an inner surface of the belt is moisture-absorbent.

9. Waist belt according to claim 1, wherein both the inner and outer surfaces of the belt consist of a non-woven material.

10. Waist belt according to claim 8, wherein the attachment means when attached to said non-woven material has a peel strength of between 0.1–2.0 $Ncm^{-1}$, and a shear strength of greater than 1 $Ncm^{-2}$, though.

11. Waist belt according to claim 1, wherein the longitudinal edges of the belt are along a major proportion of its length and the attachment means extend over a central portion of the belt width.

12. The waist belt of claim 5, wherein the one end portion width is 60% of the width of the belt.

13. The waist belt of claim 6, wherein the greatest dimension is less than 50% of the belt width.

14. The waist belt of claim 7, wherein the greatest dimension is more than 3 times the lateral extent of the attachment means.

15. The waist belt of claim 10, wherein the peel strength is between 0.2 and 0.8 $Ncm^{-1}$.

16. The waist belt of claim 10, wherein the shear strength is greater than 15 $Ncm^{-2}$.

17. The waist belt of claim 15, wherein the shear strength is greater than 15 $Ncm^{-2}$.

* * * * *